US012635994B2

(12) United States Patent
Vetter

(10) Patent No.: US 12,635,994 B2
(45) Date of Patent: May 26, 2026

(54) SOFT TISSUE FINE NEEDLE CORE BIOPSY AND SPECIMEN FIXATION DEVICES AND METHODS

(71) Applicant: TransMed7, LLC, Portola Valley, CA (US)

(72) Inventor: James W Vetter, Portola Valley, CA (US)

(73) Assignee: Transmed7 LLC, Portola Valley, CA (US)

( * ) Notice: Subject to any disclaimer, the term of this patent is extended or adjusted under 35 U.S.C. 154(b) by 436 days.

(21) Appl. No.: 18/123,504

(22) Filed: Mar. 20, 2023

(65) Prior Publication Data

US 2024/0041442 A1    Feb. 8, 2024

Related U.S. Application Data

(60) Provisional application No. 63/327,579, filed on Apr. 5, 2022.

(51) Int. Cl.
A61B 10/02 (2006.01)
A61B 10/06 (2006.01)

(52) U.S. Cl.
CPC .......... A61B 10/0283 (2013.01); A61B 10/06 (2013.01)

(58) Field of Classification Search
CPC . A61B 10/0283; A61B 10/06; A61B 10/0096; A61B 2010/0208; A61M 5/24; A61M 5/178
See application file for complete search history.

(56) References Cited

U.S. PATENT DOCUMENTS

| | | | |
|---|---|---|---|
| 5,573,008 A | 11/1996 | Robinson et al. |
| 5,980,468 A | 11/1999 | Zimmon |
| 6,322,522 B1 | 11/2001 | Zimmon |
| 9,456,807 B2 | 10/2016 | Vetter et al. |
| 9,808,226 B2 | 11/2017 | Vetter |

(Continued)

FOREIGN PATENT DOCUMENTS

WO    2022051601 A1    3/2022

OTHER PUBLICATIONS https://www.cardinalhealth.com/en/product-solutions/medical/laboratory-products/specimen-collection-kits/tissue-biopsy-kits.html , downloaded on Jun. 2, 2023.

(Continued)

*Primary Examiner* — Jeffrey G. Hoekstra
(74) *Attorney, Agent, or Firm* — YOUNG LAW FIRM. P.C.

(57) ABSTRACT

A device may comprise a collection tube comprising an interior surface defining an interior space, the collection tube comprising a first end and a second end defining a luer; a tissue collection magazine received within the interior space of the collection tube; a sealing cap comprising a first end configured to receive one end of the tissue collection magazine and couple to the first end of the collection tube, the sealing cap comprising a second end configured to selectively receive one of a work element of a biopsy device, a vacuum source and a source of a fluid; and a tube-shaped mesh screen disposed within the tissue collection magazine and facing the interior surface, the tube-shaped mesh screen comprising an open end closest to the sealing cap and a closed end furthest away from the sealing cap.

10 Claims, 7 Drawing Sheets

(56) References Cited

U.S. PATENT DOCUMENTS

| 10,076,315 | B2 | 9/2018 | Vetter et al. |
| 10,555,751 | B2 | 2/2020 | Vetter et al. |
| 11,234,684 | B2 | 2/2022 | Vetter et al. |
| 11,504,101 | B1 | 11/2022 | Keller et al. |
| 2002/0082519 | A1 | 6/2002 | Miller et al. |
| 2004/0049128 | A1 | 3/2004 | Miller et al. |
| 2004/0161788 | A1 | 8/2004 | Chen et al. |
| 2005/0027210 | A1 | 2/2005 | Miller |
| 2005/0165329 | A1 | 7/2005 | Taylor et al. |
| 2009/0204020 | A1 | 8/2009 | Miller et al. |
| 2009/0287190 | A1* | 11/2009 | Shippert ............... A61M 1/604 |
| | | | 604/542 |
| 2011/0257557 | A1 | 10/2011 | Pesce |
| 2012/0065542 | A1 | 3/2012 | Hibner |
| 2012/0116246 | A1 | 5/2012 | Hibner et al. |
| 2012/0150145 | A1* | 6/2012 | Cucin ................... A61M 1/892 |
| | | | 604/506 |
| 2012/0157879 | A1 | 6/2012 | Mark |
| 2015/0209017 | A1 | 7/2015 | Fleming et al. |
| 2016/0183928 | A1 | 6/2016 | Speeg et al. |
| 2016/0235391 | A1 | 8/2016 | Gardner et al. |
| 2016/0249892 | A1 | 9/2016 | Gardner et al. |
| 2018/0221003 | A1 | 8/2018 | Hibner et al. |
| 2019/0110779 | A1 | 4/2019 | Gardner et al. |
| 2019/0133561 | A1 | 5/2019 | Videbaek et al. |
| 2019/0321009 | A1 | 10/2019 | Nevo et al. |
| 2020/0187922 | A1 | 6/2020 | Toft et al. |
| 2022/0313227 | A1 | 10/2022 | Rebellino et al. |

OTHER PUBLICATIONS

Lott, Robert et al., Practical Guide to Specimen Handling in Surgical Pathology, National Society for Histotechnology, College of American Pathologists, Version 10.0, Revised Jul. 2022 (72 pages).
Written Opinion of the international Searching Authority dated Jul. 27, 2023 in PCT/US2023/015634.
Extended European Search Report of Nov. 27, 2025 in EP Application 23785164.7 (8 pages).

* cited by examiner

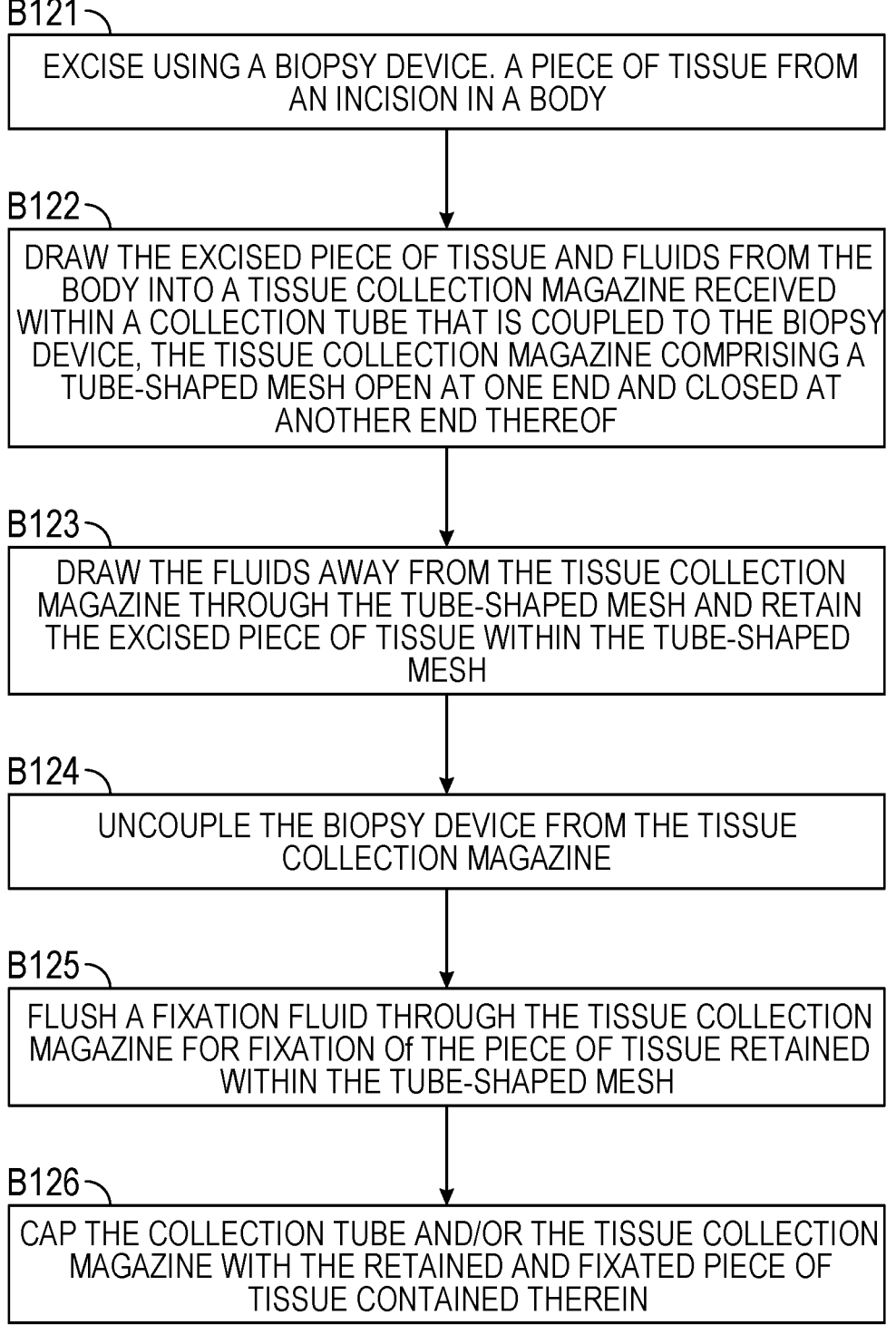

B121
EXCISE USING A BIOPSY DEVICE. A PIECE OF TISSUE FROM AN INCISION IN A BODY

B122
DRAW THE EXCISED PIECE OF TISSUE AND FLUIDS FROM THE BODY INTO A TISSUE COLLECTION MAGAZINE RECEIVED WITHIN A COLLECTION TUBE THAT IS COUPLED TO THE BIOPSY DEVICE, THE TISSUE COLLECTION MAGAZINE COMPRISING A TUBE-SHAPED MESH OPEN AT ONE END AND CLOSED AT ANOTHER END THEREOF

B123
DRAW THE FLUIDS AWAY FROM THE TISSUE COLLECTION MAGAZINE THROUGH THE TUBE-SHAPED MESH AND RETAIN THE EXCISED PIECE OF TISSUE WITHIN THE TUBE-SHAPED MESH

B124
UNCOUPLE THE BIOPSY DEVICE FROM THE TISSUE COLLECTION MAGAZINE

B125
FLUSH A FIXATION FLUID THROUGH THE TISSUE COLLECTION MAGAZINE FOR FIXATION Of THE PIECE OF TISSUE RETAINED WITHIN THE TUBE-SHAPED MESH

B126
CAP THE COLLECTION TUBE AND/OR THE TISSUE COLLECTION MAGAZINE WITH THE RETAINED AND FIXATED PIECE OF TISSUE CONTAINED THEREIN

FIG. 12

SOFT TISSUE FINE NEEDLE CORE BIOPSY AND SPECIMEN FIXATION DEVICES AND METHODS

BACKGROUND

Embodiments relate to medical devices and methods. More particularly, embodiments relate to hand-held or mounted single insertion, single or multiple soft tissue biopsy or material retrieval devices and corresponding methods for sampling and preserving materials such as soft tissue samples. Embodiments further relate to improvements over currently used fine needle aspiration systems, specifically in providing minimally invasive and more reliable vacuum assisted fine needle core biopsy and tissue preservation devices and methods.

SUMMARY

Embodiments are drawn to various medical devices and methods that are used for aspiration and soft tissue biopsy procedures, as well as structures and functionality for preserving acquired tissue samples for later pathology analysis. According to one embodiment, a soft tissue aspiration and/or core biopsy device may be configured to remove liquids, semi-solids and single or multiple biopsy samples during a single insertion through the skin (percutaneous procedure) in any soft tissue area of the body. Embodiments may comprise structures and functionality for different phases of a multi-phase biopsy procedure, which may be performed by hand or by device attachment to a stereotactic table stage or Magnetic Resonance Imaging (MRI) stage. Embodiments of a soft tissue biopsy device, along with associated related subcomponents described herein, may provide the capability to retrieve solid, contiguous and/or fragmented soft tissues as well as liquid and semi-solid tissues for analysis, diagnosis and treatment and exhibit improvements in functionality and performance relative to present devices and methods for carrying out fine needle aspiration and fine needle core biopsy sampling. Embodiments may be configured to be portable, disposable or reusable and may be, for example, electrically-, mechanically-, and/or manually-powered and operated.

BRIEF DESCRIPTION OF THE DRAWINGS

FIG. 12 is a flowchart of a method for fixating tissue contained in a tissue collection chamber remaining with a soft tissue biopsy device, according to one embodiment.

DETAILED DESCRIPTION

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

According to embodiments, a device 10 for soft tissue biopsy or combined soft tissue biopsy and tissue specimen fixation may be configured to collect and remove tissue or other materials from the body and may have a range of work element diameters ranging from, for example, approximately 22 gauge to 8 gauge, or other appropriate dimensions. The term "work element" or "work element 13" as used in this description refers to the distal end of a biopsy device 10 which penetrates an open lumen such as a natural body cavity or airway, or through tissue to remove target tissue, as well as tissue fragments, and other solids and liquids. Such work element 13 may be of rigid or flexible construction, according to various embodiments herein. The work element may comprise, in different implementations, a coring biopsy device, a mechanically-articulated cutting device, a side-cutting device configured to cut invaginated tissues, a morcellating biopsy device or any device that is configured to cut, scrape, tear, nibble and/or aspirate tissue or cells or fluids from the body. Cryogenic and RF-based biopsy devices may also be used as the "work element". According to embodiments, a simple device 11, which may be considered a subset of device 10, for fixation of tissue collected by a biopsy device, either the biopsy device 10 described in this specification or another device that has compatible tissue collection and transport elements similar to those described for the biopsy device 10 or 11 herein, may advantageously allow for tissue bathing and immediate fixation with a formalin-containing solution post-biopsy collection if the tissue is still contained in a tissue collection magazine inside a collection tube, such as a hypodermic syringe barrel, according to embodiments and methods herein.

Figures 1, 2:
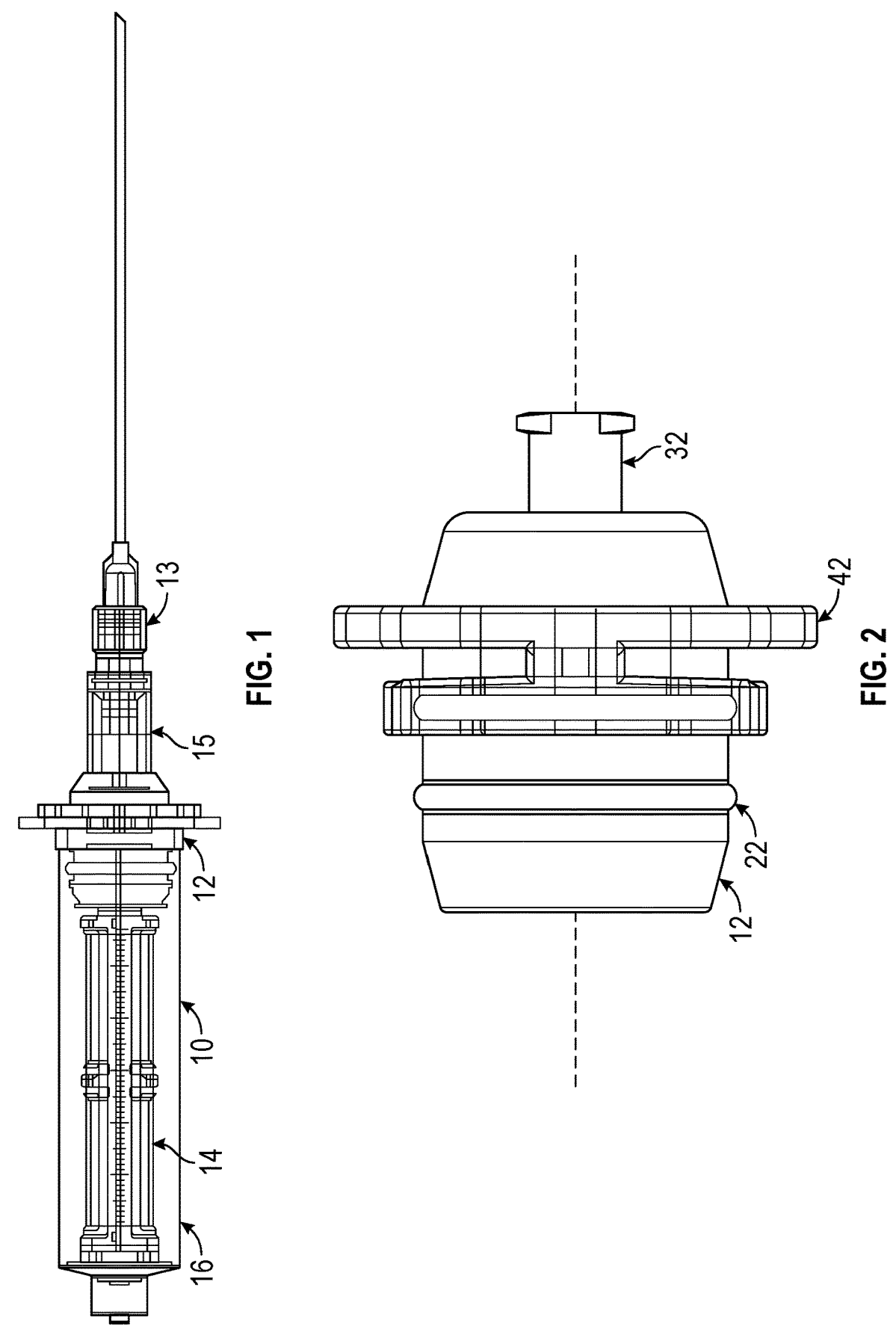
FIG. 1 is a perspective side view of a combined soft tissue biopsy and tissue specimen fixation device, according to one embodiment.
FIG. 2 is a side view of a sealing cap with open central lumen, according to one embodiment.

FIG. 1 shows one embodiment of a combined biopsy and soft tissue sample fixation device 10, with various component elements such as a sealing cap 12, a tissue collection magazine 14, a standard syringe barrel 16 with male luer connection, a generic luer adapter 15, and a distal work element 13 such as a hypodermic needle or other work element, according to embodiments. The component elements that make up the biopsy, material retrieval or combined biopsy and tissue fixation device 10 are discussed further below.

FIG. 2 is a side view of a sealing cap 12 with open central lumen, denoted by dashed lines, according to one embodiment. Such a sealing cap 12 may be of various sizes, and made of, for example, injection molded plastic such as polycarbonate or other polymer, or may be machined from billet stock. This sealing cap may feature one or more sealing "O" rings 22 about its circumference, configured to seal against the inner wall of a standard syringe barrel 16 as shown in FIG. 1, and of various sizes matched to the corresponding mating size of such a compatible sealing cap 12. The sealing cap 12 may also feature a standard luer connection 32, male or female (female shown in FIG. 2), at its outer or distal end, and may also feature wings 42 with slots configured to fit over the wings of a standard syringe barrel 16's proximal end to lock it to the syringe barrel 16, according to embodiments. The luer connector 32 at the distal end of the sealing cap 12 may be connected to either a work element 13, such as a hypodermic needle or other work element as described herein, or to a vacuum source, or to a fluid source such as a flask of formalin or other solution, such sources being equipped with a compatible luer connector capable of connecting it to the sealing cap 12's distal luer connector 32, according to embodiments and methods described herein. The sealing cap 12 is configured to replace the plunger of a standard syringe to provide novel functionality and advantages for fine needle aspiration or soft tissue biopsy than a standard complete syringe with plunger and needle tip, according to embodiments.

Figures 3, 4:
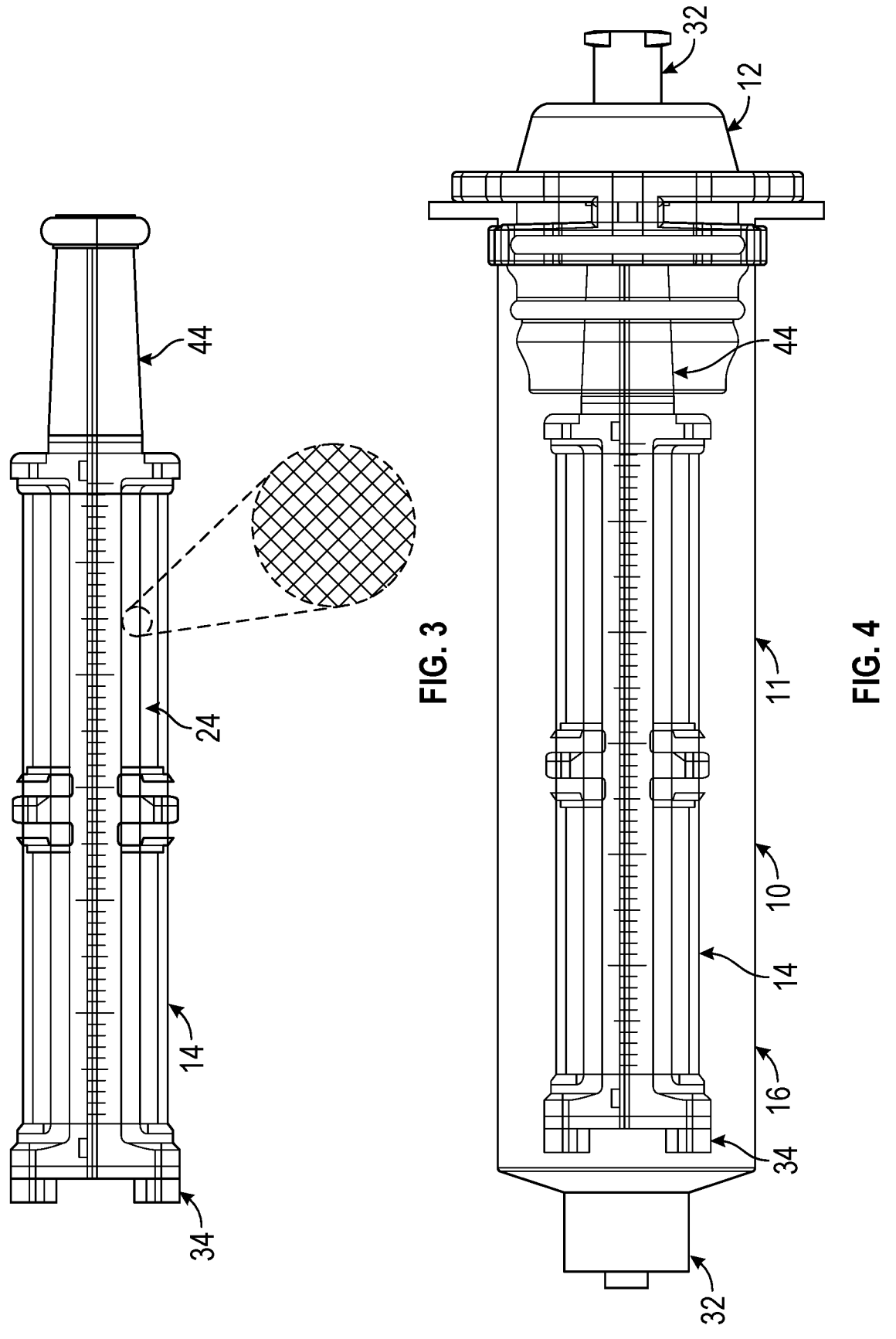
FIG. 3 is a side view of a tissue collection chamber or magazine, according to one embodiment.
FIG. 4 is a side view of a tissue sample fixation device, according to one embodiment.

FIG. 3 is a side view of a tissue collection chamber or magazine 14, according to one embodiment. Such a tissue collection chamber element 14 may, according to one embodiment, include a clam-shell structure featuring a longitudinally disposed body with incorporated fine screen mesh 24 as or at its outer circumference. The fine mesh screen 24 may be closed at the proximal end 34 thereof and open at the distal end thereof to receive tissue and fluids through an extension 44, according to one embodiment. Such a tissue collection magazine 14 may be constructed in various sizes to fit inside various corresponding sizes of standard syringe barrels, such that it may receive collected tissue and fluids at its distal end, and then allow its incorporated fine screen mesh 24 to contain solid tissue segments and fragments in its central lumen while allowing liquids to be drawn through its mesh screen and evacuated out of the syringe barrel in which it is placed, according to one embodiment.

FIG. 4 is a side view of a biopsy device 10 as shown in FIG. 1, but with its work element 13 removed, according to one embodiment. FIG. 4 may also represent a simple tissue sample fixation device 11 as a subset of device 10, including a standard syringe barrel 16 with a tissue collection chamber or magazine 14 installed inside the syringe barrel, and a sealing cap 12 shown replacing the syringe's plunger, according to one embodiment. In this instance, the tissue collection magazine 14 is placed inside the syringe barrel 16 with the proximal or closed end 34 of the tissue collection magazine closest to the luer connection or distal end of the syringe barrel 16 itself, according to one embodiment. The sealing cap 12 may be placed over the distal or outer open end of the tissue collection chamber 14, which is held in the open central lumen of sealing cap 12. Sealing cap 12 may then be placed into the proximal end of the syringe barrel 16, so as to mate with the syringe barrel 16, seal against its inner surface, and contain the tissue collection magazine enclosed within, according to one embodiment. The open end 44 of the tissue collection magazine 14 may closely fit the internal opening of sealing cap 12's open end in order to receive and collect samples taken by the work element 13 attached to sealing cap 12 in a biopsy procedure. Thus, the combination of syringe barrel 16, tissue collection magazine 14 and sealing cap 12 is structured as a closed tissue and liquid containment or strainer system, open at each end of such a device 11. The open ends of such a device 11 may consist of luer connectors 32 (one on each end of the sample fixation device 11) for easy connection of accessories, such as formalin flush systems which may allow formalin to flow over any captured specimens in the tissue collection magazine 14 and out the opposite side of device 11, according to one embodiment. If a simple biopsy device has been used to take liquid or solid or fragmented tissue samples from a target site, once its work element 13, in whatever form that may take, is removed, biopsy device 10 becomes tissue fixation device 11, according to one embodiment. If a different biopsy device other than device is used for tissue sampling, if such alternate biopsy device is fitted with a tissue collection magazine similar to that described herein, and if further such alternate biopsy device uses a standard syringe as its tissue collection tube, then a sealing cap 12 may be fixed to that tissue collection tube with contained tissue collection magazine for purposes of immediately fixating the contained tissue specimens with a formalin flush, as described above, and according to one embodiment. According to still further embodiments, a sealing cap 12 and a syringe barrel 16, with a simple fine mesh screen inserted first into syringe barrel 16 at its luer end may be used as a fixation device 11. In this manner, tissue samples obtained from any biopsy device may be placed into syringe barrel 16 with its fine mesh screen, the sealing cap 12 may be attached to the syringe barrel 16 and appropriate luer tubing may be placed at either end of fixation device 11, whereupon a formalin solution may be flushed through fixation device 11 to preserve the tissue samples, and finally, luer caps may be placed at each end of fixation device 11 for transport of the device with tissue samples to a pathology laboratory for histological analysis.

According to one embodiment, a work element 13, such as a needle, may be placed at either end of device 10 for purposes of taking tissue or liquid samples. If the work element 13 is place at the syringe barrel 16's luer connection 32, the tissue collection magazine 14 may simply be turned around so that when placed into the syringe barrel, its open end 44 is at the syringe barrel's luer end 32 with its connected needle work element in order to receive tissue samples aspirated into the device 10 as it is being used for soft tissue biopsies. This placement may be seen to be opposite to that described in FIG. 4 above. In such embodiment, sealing cap 12 would be placed over the closed end 34 of tissue collection magazine 14, sealing it inside the syringe barrel 16. In such case, device 10's sealing cap 12 would correspond to device 10's proximal end, and the sealing cap 12 luer connection 32 may thus be connected to an external suitable vacuum and liquid containment source, according to embodiments.

Figures 5, 6:
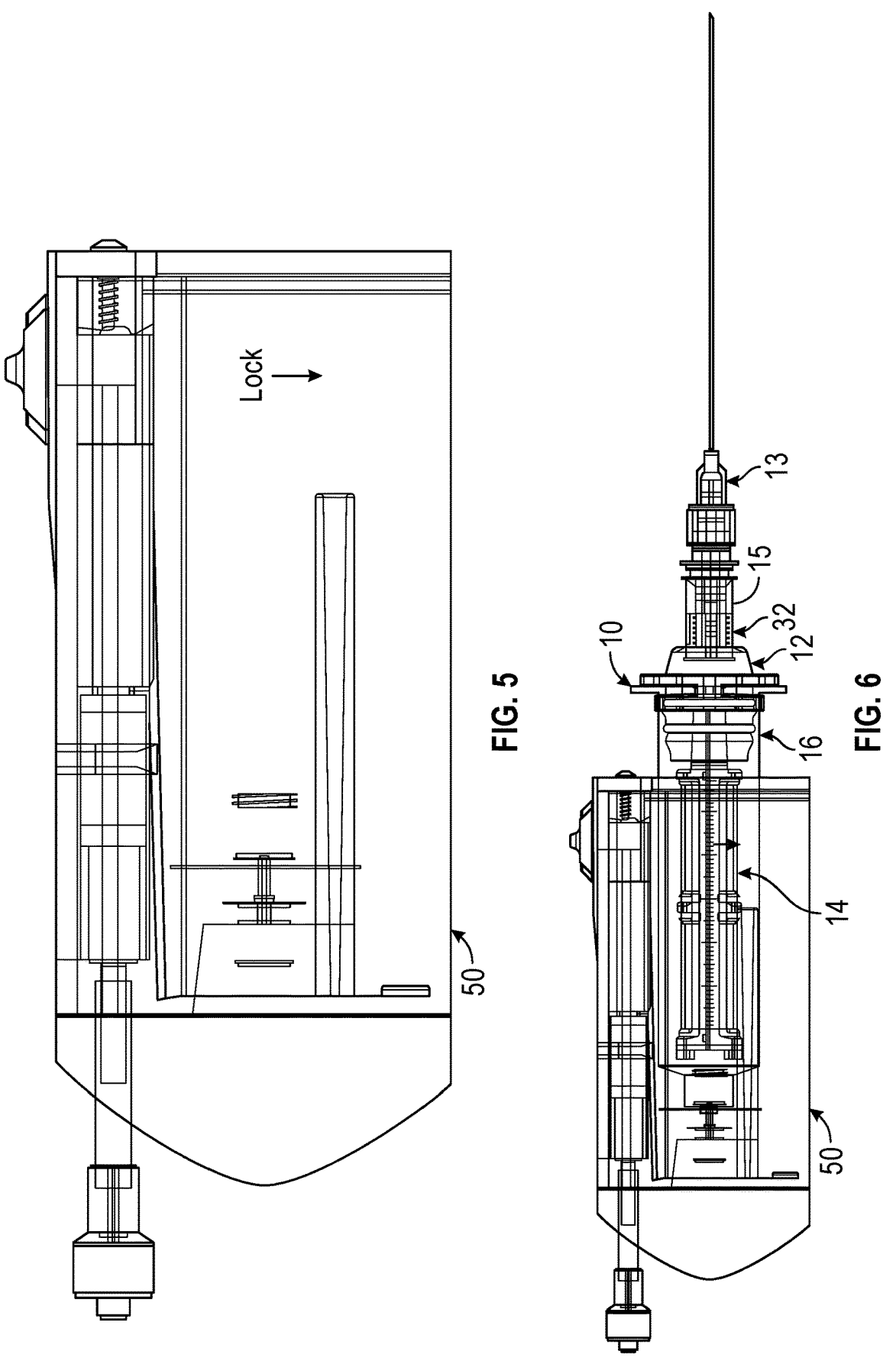
FIG. 5 is a side view of a self-contained, battery powered vacuum and liquid collection device which may be used with a tissue collection device, according to one embodiment.
FIG. 6 is a side view of an assembled soft tissue biopsy device with a self-contained vacuum and liquid collection device placed over it, according to one embodiment.

FIG. 5 is a side view of a self-contained, battery powered vacuum and liquid collection device 50, which may be used with a tissue collection device 10 as described herein, according to one embodiment. Such a vacuum and liquid collection device 50 may thus constitute a vacuum source and liquid containment source for a biopsy device 10, allowing any fluid collected during a biopsy procedure to be contained in the vacuum device and conserved for later cytology analysis, as desired. An exemplary one of such a self-contained vacuum and liquid collection device 50 is described in U.S. Pat. No. 11,234,684, which is incorporated herein by reference in its entirety. Other vacuum devices, however, may be used in conjunction with the embodiments described herein. Indeed, it should be noted that any vacuum source, whether a different vacuum pump, wall suction or other vacuum and liquid containment system used in conjunction with ordinary biopsy procedures may also be used with device 10 by simple connection to device 10's syringe barrel luer connection 32, according to further embodiments. Such an external vacuum/liquid collection system may even include another complete syringe, mated to the device 10's syringe barrel luer connection 32 with an appropriate luer adapter 15, according to another embodiment.

FIG. 6 is a side view of a biopsy device 10 incorporating a self-contained vacuum and liquid collection system as an element of device 10. In this view, an assembled syringe barrel 16, tissue collection magazine 14, and sealing cap 12 with its distal luer connector 32 is connected to a hypodermic needle, additionally with a self-contained vacuum and liquid collection device 50 placed over the syringe barrel 16, according to one embodiment. The self-contained vacuum and liquid connection device 50 may be configured to mate to the luer end 32 of the syringe barrel 16, and thus provide vacuum to the central lumen of device 10, according to embodiments. Different luer connectors or adapters 15 may be attached to either end of device 10 in order to add additional capabilities, such as external valves to control input or egress of various substances into device 10 or device 11, at various stages of such devices use, according to further embodiments. According to another embodiment, device 10, in either configuration, may have a long flexible tube as the work element 13 or as part of the work element 13, for purposes such as aspirating and collecting liquids and semi-solids from, for example, deep regions of the lung for cytology and histology analyses, according to methods.

One embodiment of the present material delivery or removal device 10, as shown in the figures, may be implemented in a hand-held configuration comprising an ergonomically comfortable assembled unit, as shown in FIG. 6. Work element 13 may extend from the device 10 so that the device 10 may be easily grasped, directed and operated with one hand while the other hand is free to hold a guiding probe such as an ultrasound transducer. Additionally, if the hand holding device 10 is allowed to rotate or cycle in partial rotation in an oscillating motion, the work element 13 may be more efficient in collecting and severing targeted tissue during a biopsy procedure, according to methods.

However, it is to be understood that embodiments of device 10 may readily be configured to fit onto any number of guiding devices such as a stereotactic imaging stage or other guidance modality such as that of an MRI. The entire device 10 may be configured to be disposable or may be configured to be reusable in whole or in part.

Figure 7:
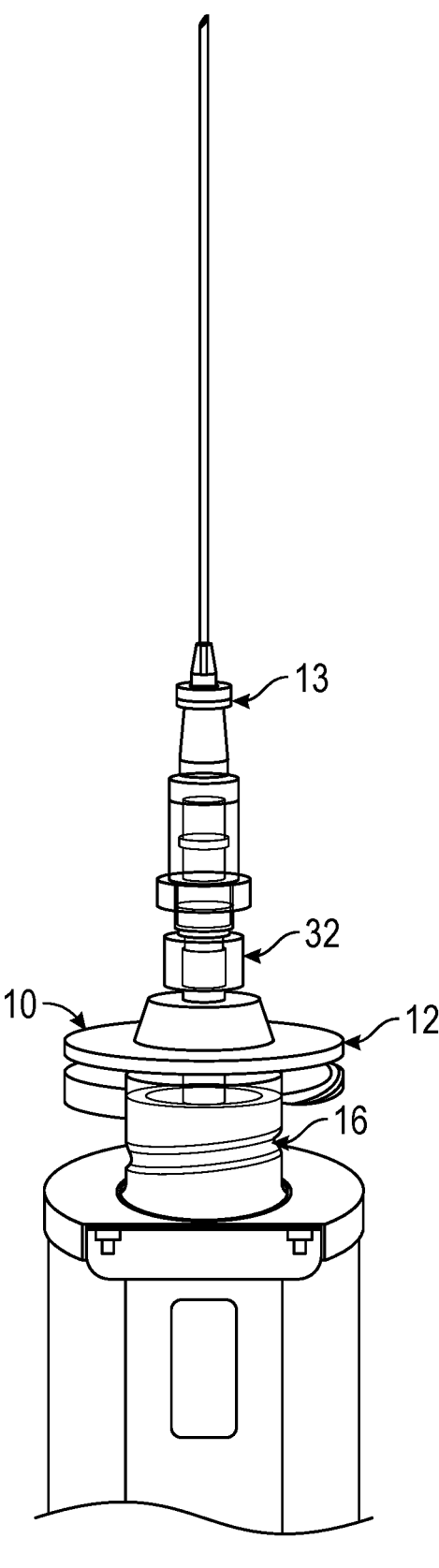
FIG. 7 is a close-up view of the distal end of a biopsy device, according to one embodiment.

FIG. 7 is a close-up view of the distal end of a biopsy device 10, according to one embodiment. In this view, sealing cap 12 may be seen placed over the proximal, wing end of a standard syringe barrel 16, with a work element 13, in this case a standard luer hypodermic needle, attached to the luer connector 32 of the sealing cap 12. Such attachment of the work element 13 to sealing cap 12 may be in the form of any of a number of standard luer connectors 15 (shown in FIG. 1), including swiveling luer connector adapters, according to embodiments.

Figures 8, 9:
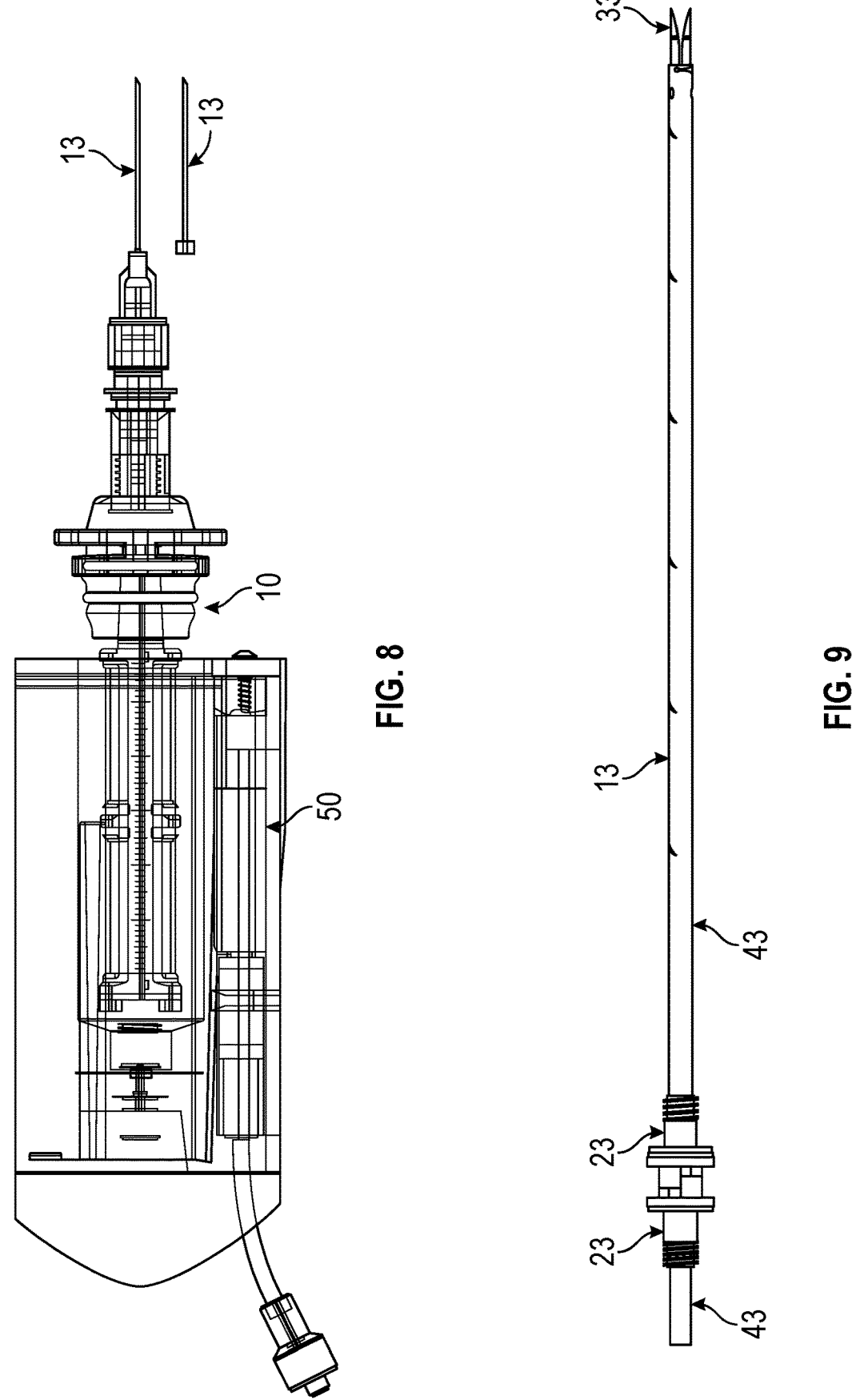
FIG. 8 is a view of a soft tissue device with alternate needle tips, according to embodiments.
FIG. 9 is a side view of a tissue collection needle set assembly, according to one embodiment.

FIG. 8 is a view of a soft tissue device shown with alternate standard luer needle tips as work elements 13, according to embodiments. Such needle tips may be of Chiba- or Franseen-type hypodermic needles or other configuration as described in FIG. 9 below, according to embodiments.

FIG. 9 is a side view of a tissue collection needle set assembly or work element 13, according to one embodiment. In this case, the work element 13 may be partially composed of, according to one embodiment, a monolithic structure formed from two or more laser-cut and welded stainless steel hypo-tubes. According to embodiments, such a work element 13 may include a single inner tube at least partially disposed within a coaxially-disposed outer tube. Such a stainless-steel inner hypo tube, according to one embodiment, may be provided with (e.g., laser) cuts to define a monolithic distal assembly that defines one or more work elements such as beaks 33, a living hinge that attaches the beak(s) to the generally tubular body of the device or that homogeneously spans between the beak(s) and the generally tubular body of the device. According to one embodiment, cuts in the hypo tube may define one or more tendons configured to actuate the beak(s) 33. The cuts in the hypo tube may also define one or more tendon actuation tabs that enable actuation (e.g., opening and closing) the beak(s) through the tendons and limit the travel thereof. The tendon actuator tab(s) may be located at any location along the length of the hypo tube. The coaxially-disposed outer tube 43, according to one embodiment, may comprise one or more coatings. According to one embodiment, the outer tube 43 may comprise a stainless-steel hypodermic tubing ("hypotube"). The device may also be made of materials other than stainless-steel, such as plastics or other suitable materials, which may incorporate the features of the beak(s), tendon(s), and, according to embodiments, tendon actuation tab(s) or an internal tube actuator element. Such a work element 13, according to one embodiment, is described and may be found in U.S. Pat. Nos. 10,555,751; 9,808,226; 10,076,315 and 9,456,807, which are incorporated herein by reference. As noted elsewhere in this disclosure, the work element may include configurations other than that described in these patent numbers and described herein, as the device according to the embodiments described herein is agnostic as to the kind of work element used to separate and collect tissue from the body.

Such a work element 13 as described in the cited US patents above, may comprise three hypotubes (elements 33, 43 and 53 as shown in this figure), laser cut in specific patterns and welded to each other to form assembled work element 13. As described in the referenced patents, such a work element 13 may further include of an innermost short beak element featuring twin beaks 33 attached to tendons used to actuate the twin beak opening and closing motions by relative axial movement of the tendons with relation to the main body of the beak element, and a coaxially surrounding inner tube laser welded to the base of the beak element and an outermost coaxial tube welded to the base of the tendons. Such a structure allows for beak element beaks opening and closing by relative axial movement of the inner and outermost tubes, according to embodiments. Such a work element 13 attached to the sealing cap 12 of device 10, with the inner tube 53 of the work element extending through the distal end of sealing cap 12 to the tissue collection magazine 14 through its open end 44 of device 10, allows tissue collection by device 10 by inserting the work element into tissue, rotating or oscillating in partial rotation the open beaks of the beak element of work element 13, and then simply grasping and pulling proximally the outer tube of the work element to close the beaks and part off the cored tissue sample, according to methods. The cored tissue sample thus obtained may then be transported proximally the length of work element 13 and into the tissue collection magazine 14 of device 10, according to embodiments. The dog elements 23 of such a work element 13 allow for synchronous rotation of the entire work element while allowing relative axial movement of the outer tube in relation to the inner tube of the work element to open and close the beaks, with coring occurring efficiently with open beaks in rotation moving through soft tissue to be sampled in a biopsy procedure.

Figures 10, 11:
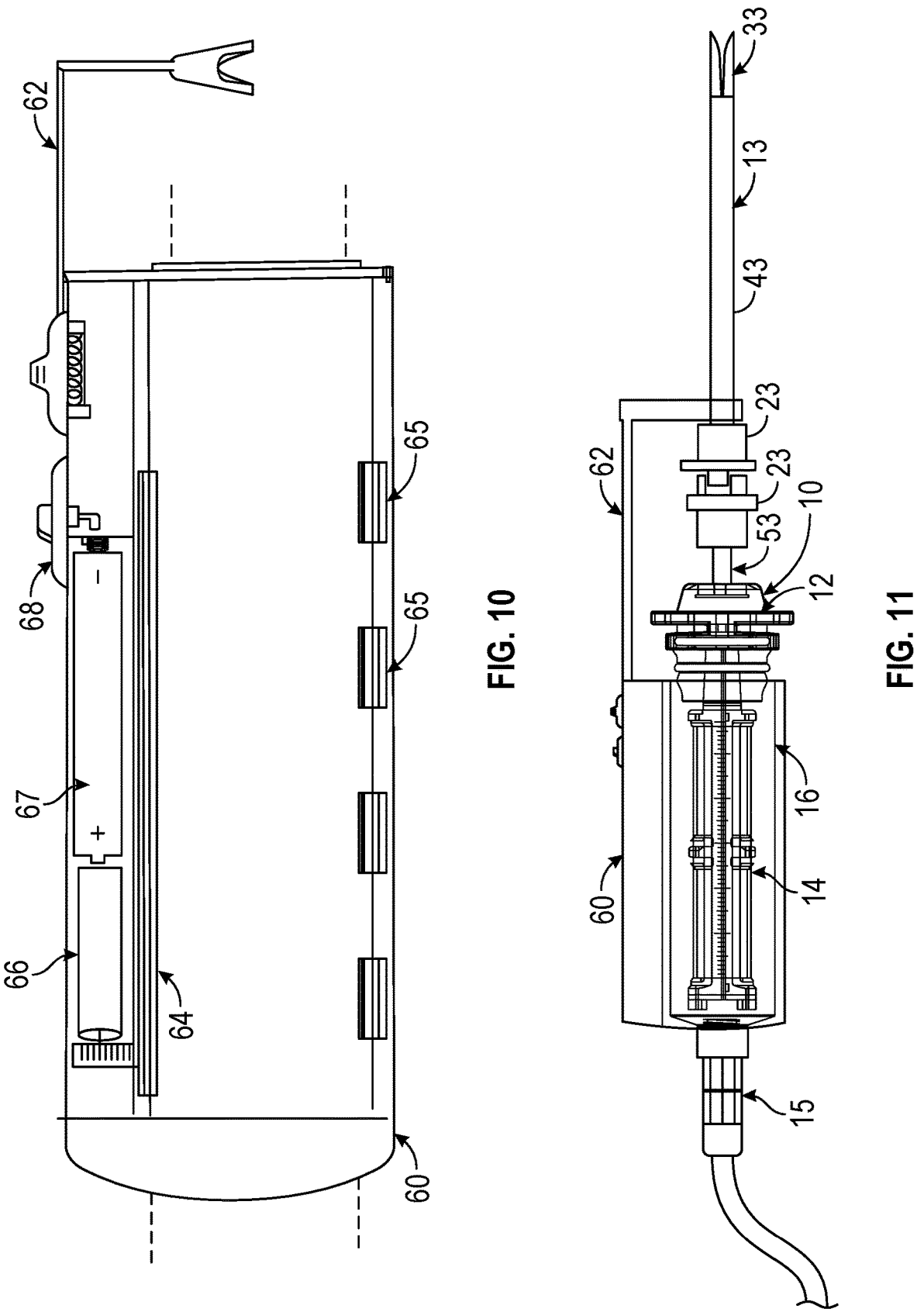
FIG. 10 is a view of a motor-operated powered rotator and control mechanism for a soft tissue biopsy device, according to one embodiment.
FIG. 11 is a view of a motor operated powered rotator and control mechanism installed over a soft tissue biopsy device, according to one embodiment.

FIG. 10 is a view of a motor-operated powered rotator and control mechanism 60 for a soft tissue biopsy device 10, according to one embodiment. Such a rotator mechanism 60 may be configured to be placed over the syringe barrel 16 of a device 10, similar to the placement of element 50 described above in FIGS. 5 and 6 over device 10. In this case, rotator mechanism 60 placed over syringe barrel 16 (syringe barrel 16 location inside rotator mechanism 60 is denoted by short, dashed lines in this figure) may include an internal electric motor-powered driving roller 64 with opposite passive rollers 65 that grasp the outer circumference of syringe barrel 16 of device 10, and thus allow for rotation of the entire device 10 inside rotator mechanism 60, according to embodiments. Rotator mechanism 60 may serve as a simple handle for an operator of device 10 and can be seen in this figure to contain a battery powered small electric motor 66 to drive driving roller 64; as well as batteries 67, and motor switch 68 allowing rotation to be turned on and off as desired by an operator, according to methods. Forward of switch 68 is a simple spring-loaded sliding forked arm element 62 that extends forward over a work element as described in the following section, which may allow an operator to selectively close work element 13's beaks 33 by pulling the sliding forked arm 62 proximally, or open beaks 33 by allowing the sliding forked arm 62 to resiliently return to its forward position as a result of its being spring-loaded to return to its initial position on rotator mechanism 60, according to one embodiment.

FIG. 11 is a view of a motor operated powered rotator and control mechanism 60 installed over a soft tissue biopsy device 10, according to one embodiment. In this view, the device 10 with its assembled elements is placed inside of a powered rotator and control mechanism 60 in such manner as to allow device 10 to be rotated in its entirety, including its work element 13. FIG. 11 shows the work element of FIG. 9. As shown, the inner tube 53 has been inserted through the distal end of sealing cap 12 and into tissue collection magazine 14 placed inside syringe barrel 16, according to one embodiment. As also shown, the dogs 23 of work element 13 are exposed outside of the open end of sealing cap 12, thus allowing for opening and closing of the beaks 33 by relative axial motion between work element 13's inner tube 53 and outer tube 43. This relative motion is induced by pulling the exposed distal dog 23 towards the exposed proximal dog 23 which then closes the beaks 33 for tissue penetration and parting off cored tissue specimens, according to methods. Allowing the distal dog element 23 to move to its original forward position allows the beaks 33 to reopen for coring mode of the device 10. Therefore, powered rotator and control mechanism 60 placed over the syringe barrel 16 as shown in FIG. 11 operates to rotate the entire device 10, which rotation would naturally extend to work element 13 with its beaks 33. A luer adapter 15 of the swivel type connected to the proximal end of device 10 at the syringe barrel 16's luer connection 32 and being itself connected to a flexible tube leading to a source of vacuum and liquid collection would allow for vacuum assisted cored tissue transport from the work element 13 to the tissue collection magazine 14 of device 10. As noted in the description for FIG. 10 above, rotation of device 10 induced and controlled by a powered rotator and control mechanism 60, with its sliding forked arm 62 placed over the distal dog 23 of work element 13, allows operator-controlled powered rotation as well as beak 33 closing and opening by simply pulling proximally the sliding forked arm 62 for closing or allowing it to return to its normal forward or distal position for beak opening at any point of a biopsy procedure, according to embodiments.

FIG. 12 is a flowchart of a method for fixating tissue contained in a tissue collection chamber remaining with a soft tissue biopsy device, according to one embodiment. As shown in FIG. 12, according to one embodiment, a method of carrying out a biopsy or excisional procedure may be preceded by procedures including, for example, imaging the tissue of the organ or structure of interest and identifying the target lesion(s) or tissue to be biopsied or excised. The skin may then be cleansed using sterile techniques, and the patient may be draped, and anesthetics may be delivered. The distal tip or work element 13 of the present device 10 may then be introduced through a skin nick incision. Tissue penetration to the target site may be carried out with the work element 13 in a predetermined configuration (such as, for example, an open or closed configuration; that is, the beak or beaks 33 of FIG. 9 above, for example and if used, may be open or closed), which configuration may be selected by the operator. Since the device 10, according to one embodiments, may be provided with aspiration through its central lumen, the proximally directed force generated by such suction will tend to draw cored tissue into the aforementioned central lumen, and may further facilitate the tissue being collected at the proximal end of the device 10 within the tissue collection magazine 14 after the beak(s) 33 have closed and parted off the tissue—or the tissue collected by other means.

Vacuum may be used for tissue and fluid aspiration through a connection at the proximal end of the device 10, as shown in FIG. 1. Fluid flushes containing material from the tissue site may be collected by aspiration to be discarded or saved for later cytological analysis. Fixation of the collected tissue specimens contained within the tissue collection magazine inside the syringe body may be accomplished by simply removing the work element 13 from the distal end of the device and attaching compatible luer connection tubes to either end of the device, whereupon flushing the samples inside the device 10, specifically contained inside the specimen collection magazine 14, with a formalin solution to fix the tissue samples. Luer caps placed on either end of the device 10 operate to maintain tissue immersion in the formalin solution for subsequent transport to a pathology laboratory for examination. A method according to an embodiment, therefore, may include excising, using a biopsy device, a piece of tissue from an incision in a body, as shown at B121 in FIG. 12. As shown at block B122, the excised piece of tissue and fluids from the body may be drawn into a tissue collection magazine received within a collection tube that is coupled to the biopsy device, the tissue collection magazine comprising a tube-shaped mesh open at one end and closed at another end thereof. Block B123 calls for drawing the fluids away from the tissue collection magazine through the tube-shaped mesh and retaining the excised piece of tissue within the tube-shaped mesh. Then, the biopsy device may be uncoupled from the tissue collection magazine, as shown at B124. A fixation fluid may be flushed through the tissue collection magazine for fixation of the piece of tissue retained within the tube-shaped mesh, as shown at B125. The collection tube may be capped with the retained and fixated piece of tissue contained therein, as shown at B126. Alternatively, the tissue collection magazine may be removed from the collection tube and then removed tissue collection magazine capped with the retained and fixated piece of tissue contained therein.

According to further embodiments, the method may further comprise coupling a sealing cap between the collection tube and the biopsy device. The flushing step may comprise leaving an amount of the fixation fluid within the collection tube and received tissue collection magazine. The method may further comprise sending the capped collection tube and/or the capped tissue collection magazine with the retained and fixated piece of tissue to a pathological laboratory for histologic analysis. Either or both of the drawing steps may comprise coupling a source of vacuum to the tissue collection device.

It is to be understood that the above description is but one exemplary methodology and that one or more of the steps described above may be omitted, while other steps may be added thereto, depending on the target site within the body or other operator methodologies. The order of some of the steps may be changed, according to the procedure.

In certain clinical situations, it may be desirable to introduce a solvent into an area (may be simply water or saline for example or may incorporate agents that provide local anesthetic or bleeding control agents or others) such that cells, tissue and thick, viscous liquids or semi-solids may be bathed in such a solvent in order to facilitate transport. In such a situation, it may be desirable to aspirate simultaneously with introduction of fluids for this purpose. In conjunction with the working elements of embodiments of a device described herein, a closed-chamber type syringe may be equipped with suitable valve and tubing elements to permit single plunger action to perform both functions simultaneously. This may also be accomplished with dual plunger, single syringe equipment for example.

The described embodiments may be formed of or comprise one or more biocompatible materials such as, for example, stainless steel or other biocompatible alloys, and may be made of, comprise or be coated with polymers and/or biopolymer materials as needed to optimize function(s). For example, the cutting elements (such as the constituent elements of a work element 13) may comprise or be made of hardened alloys or carbon fiber or other polymers or plastics and may be additionally coated with a slippery material or materials to thereby optimize passage through living tissues of a variety of consistencies and frictions. Some of the components may be purposely surface-treated differentially with respect to adjacent components, as may be inferred herein in reference to a transporting tubular and storage component (not shown). The various internal or external components may be made of any suitable, commercially available materials such as nylons, polymers such as moldable plastics, and others. The handle may be configured in such a way as to make it easily adaptable to one of any number of existing guiding platforms, such as stereotactic table stages. The materials used in the present material delivery or removal device may also be carefully selected from a ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present material delivery or removal device, along with readily available reed valves for switching between suction and emptying of materials such as fluids which may be suctioned by vacuum components. The fluids collected by the embodiments of the present device in this manner may then be ejected into an additional external, yet portable, liquid storage vessel connected to the tubing of the present device, for safe keeping and laboratory cellular analysis.

While certain embodiments of the disclosure have been described, these embodiments have been presented by way of example only and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A device, comprising:
   a single syringe barrel defining a longitudinal axis and comprising an interior surface defining an interior space, the single syringe barrel comprising a body, the body comprising a first end and a second end defining a luer, the syringe barrel further comprising at least one wing extending away from the first end of the body and away from the longitudinal axis;
   a tissue collection magazine received within the interior space of the single syringe barrel;
   a sealing cap comprising a first end configured to receive one end of the tissue collection magazine and couple to the first end of the single syringe barrel, the sealing cap comprising a second end configured to selectively receive one of a work element of a biopsy device, a vacuum source and a source of a fluid, the sealing cap further comprising at least one wing configured to fit over and directly contact one of the at least one wing of the single syringe barrel, and
   a tube-shaped mesh screen disposed within the tissue collection magazine and facing the interior surface, the tube-shaped mesh screen comprising an open end closest to the sealing cap and a closed end furthest away from the sealing cap.

2. The device of claim 1, wherein the single syringe barrel comprises a clam shell structure and is configured to be opened along a longitudinal axis thereof.

3. The device of claim 1, wherein the sealing cap comprises an O-ring configured to seal the first end thereof to the first end of the single syringe barrel.

4. The device of claim 1, wherein the second end of the sealing cap comprises a luer that is configured to selectively couple to the work element of a biopsy device, the vacuum source and the source of the fluid the work element.

5. The device of claim 1, wherein the fluid is a fixation fluid and wherein the device is configured to be detached from the biopsy device, at least partially filled with the fixation fluid to preserve tissue collected by the biopsy device pending examination of the collected and preserved tissue.

6. The device of claim 1, further comprising a first luer cap placed on the first end of the syringe single barrel and a second luer cap placed on the second end of the single syringe barrel.

7. The device of claim 1, configured for hand-held operation.

8. The device of claim 1, configured for attachment to a stereotactic imaging stage.

9. The device of claim 1, further comprising a powered rotator and control mechanism attached to the device and configured to rotate the work element of the biopsy device.

10. The device of claim 1, wherein each of the at least one wing of the sealing cap comprises a slot configured to fit one of the at least one wing of the single syringe barrel.

\* \* \* \* \*